United States Patent
Sell et al.

(10) Patent No.: US 7,630,840 B2
(45) Date of Patent: Dec. 8, 2009

(54) OXYGEN SENSOR READINESS DETECTION

(75) Inventors: Jeffrey A. Sell, West Bloomfield, MI (US); Bradley Gibson, Swartz Creek, MI (US)

(73) Assignee: GM Global Technology Operations, Inc.

( * ) Notice: Subject to any disclaimer, the term of this patent is extended or adjusted under 35 U.S.C. 154(b) by 197 days.

(21) Appl. No.: 11/945,565

(22) Filed: Nov. 27, 2007

(65) Prior Publication Data

US 2009/0133464 A1 May 28, 2009

(51) Int. Cl.
*G01R 31/312* (2006.01)
*G01R 31/315* (2006.01)
*G01R 31/08* (2006.01)

(52) U.S. Cl. .............. 702/58; 702/57; 702/59
(58) Field of Classification Search .......... 702/57, 702/58, 59, 64
See application file for complete search history.

(56) References Cited

U.S. PATENT DOCUMENTS

| | | | | |
|---|---|---|---|---|
| 4,332,225 A | * | 6/1982 | Cox et al. ............... | 123/697 |
| 4,742,808 A | * | 5/1988 | Blumel et al. ........... | 123/688 |
| 5,588,417 A | | 12/1996 | Kotwicki et al. ........ | 123/697 |
| 5,669,219 A | * | 9/1997 | Schnaibel et al. ....... | 60/274 |
| 6,084,418 A | * | 7/2000 | Takami et al. ........... | 324/717 |
| 6,831,471 B2 | * | 12/2004 | Gertiser et al. .......... | 324/693 |
| 7,149,609 B2 | * | 12/2006 | Hashimoto ............... | 701/1 |
| 7,282,927 B1 | * | 10/2007 | Burkatovsky ............ | 324/667 |
| 2004/0193988 A1 | * | 9/2004 | Saloio ...................... | 714/742 |
| 2008/0073551 A1 | * | 3/2008 | Dzengeleski et al. .... | 250/398 |
| 2008/0103705 A1 | * | 5/2008 | Hammerschmidt ...... | 702/57 |

* cited by examiner

*Primary Examiner*—David A. Rogers
(74) *Attorney, Agent, or Firm*—Harness, Dickey & Pierce, P.L.C.

(57) ABSTRACT

An oxygen sensor readiness module comprises a voltage source, a current detection module, and a control module. The voltage source selectively produces a bias signal, which is applied to a sensing element of an oxygen sensor. The current detection module measures a pumping current of the oxygen sensor. The control module generates a readiness signal based upon a comparison of the pumping current with a pumping current threshold.

22 Claims, 6 Drawing Sheets

OXYGEN SENSOR READINESS DETECTION

FIELD

The present disclosure relates to determining readiness of an oxygen sensor in a vehicle.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Referring now to FIG. 1, a functional block diagram of an engine system 100 is presented. Air is drawn into an engine 102 through an intake manifold 104. A throttle valve 106 varies the volume of air drawn into the engine 102. The air mixes with fuel from one or more fuel injectors 108 to form an air-fuel mixture. The air-fuel mixture is combusted within one or more cylinders 109, and resulting exhaust gas is expelled from the cylinder 109 into an exhaust system 110.

The exhaust system 110 includes an oxygen sensor 120 that includes a sensing element. A voltage forms at the sensing element based upon the concentration of oxygen in the exhaust gas. This voltage is output from the oxygen sensor 120. The oxygen sensor 120 may include a heater that receives power from a heater power supply 122. The heater may bias the oxygen sensor 120 to within an operating temperature range.

An engine control module (ECM) 124 receives the output of the oxygen sensor 120 and may receive signals from other sensors 126. The other sensors 126 may include, for example, a mass air flow (MAF) sensor, a manifold absolute pressure (MAP) sensor, and a throttle position sensor (TPS). The ECM 124 regulates the air-fuel mixture based upon the output of the oxygen sensor 120 and the signals from the other sensors 126.

In various implementations, the ECM 124 may regulate the air-fuel mixture by instructing the throttle valve 106 to increase/decrease the volume of air drawn into the engine 102. The ECM 124 may also regulate the air-fuel mixture by instructing the fuel injector 108 to increase/decrease the fuel content of the air-fuel mixture. In various implementations, the ECM 124 regulates the air-fuel mixture to maintain a stoichiometric air-fuel ratio.

The output of the oxygen sensor 120 may be unreliable until the temperature of the oxygen sensor 120 reaches a temperature threshold. The temperature threshold may be the lowest temperature within the operating temperature range. When the output of the oxygen sensor 120 is unreliable, the ECM 124 may regulate the air-fuel mixture without considering the output of the oxygen sensor 120. The temperature of the oxygen sensor 120 is likely below the temperature threshold upon starting the engine 102. Accordingly, the output of the oxygen sensor 120 is likely unreliable upon starting the engine 102.

The ECM 124 may estimate that the output of the oxygen sensor 120 will be reliable when a timer expires after the output leaves a calibratable voltage window. For example, the ECM 124 may estimate that the output of the oxygen sensor 120 will be reliable twenty (20) seconds after the output leaves a voltage window between 200 mV and 600 mV. In such implementations, the ECM 124 may estimate that the output of the oxygen sensor 120 will be reliable approximately thirty-five (35) seconds after starting the engine 102.

SUMMARY

An oxygen sensor readiness module comprises a voltage source, a current detection module, and a control module. The voltage source selectively produces a bias signal, which is applied to a sensing element of an oxygen sensor. The current detection module measures a pumping current of the oxygen sensor. The control module generates a readiness signal based upon a comparison of the pumping current with a pumping current threshold.

In other features, an oxygen sensor system comprises the oxygen sensor readiness module, the oxygen sensor, and an engine control module. The engine control module selectively uses an output of the sensing element of the oxygen sensor. In further features, the engine control module uses the output based upon the readiness signal.

In still further features, the engine control module ignores the output until the engine control module receives said readiness signal. The oxygen sensor system further comprises a switching module. The switching module connects the sensing element of the oxygen sensor to the engine control module based upon the readiness signal. The engine control module uses the output after the bias signal no longer appears at the sensing element of the oxygen sensor. The engine control module uses the output in performing closed-loop control of an air-fuel mixture.

In other features, the oxygen sensor is a switching oxygen sensor. In still further features, the oxygen sensor is one of a planar type switching oxygen sensor and a conical type switching oxygen sensor. The oxygen sensor readiness module further comprises a switching module that applies the bias signal to the sensing element of the oxygen sensor until the readiness signal is received. The oxygen sensor readiness module further comprises a clamping device that limits at least one of said bias signal and said pumping current.

In further features, the pumping current threshold is set to correspond to a temperature at which an output of the sensing element of the oxygen sensor is reliable. In still further features, the bias signal is a direct current (DC) voltage. The voltage source stops producing the bias signal after the readiness signal is received.

A method of determining readiness of an oxygen sensor, comprises selectively producing a bias signal, applying the bias signal to a sensing element of an oxygen sensor, measuring a pumping current of the oxygen sensor, comparing the pumping current with a pumping current threshold, and generating a readiness signal based upon the comparison.

In further features, the method further comprises selectively using an output of the oxygen sensor in controlling an engine based upon the readiness signal. The method further comprises ignoring an output of the oxygen sensor until the readiness signal is generated. The method further comprises connecting the sensing element of the oxygen sensor to an engine control module based upon the readiness signal.

In other features, the method further comprises using an output of the oxygen sensor in controlling an engine after the bias signal no longer appears at the sensing element of the oxygen sensor. The method further comprises applying the bias signal to the sensing element of the oxygen sensor until the readiness signal is generated. The method further comprises limiting at least one of the bias signal and the pumping current. The method further comprises stopping producing the bias signal after the readiness signal is generated.

Further areas of applicability of the present disclosure will become apparent from the detailed description provided hereinafter. It should be understood that the detailed description and specific examples, while indicating the preferred embodi-

BRIEF DESCRIPTION OF THE DRAWINGS

The present disclosure will become more fully understood from the detailed description and the accompanying drawings, wherein.

DETAILED DESCRIPTION

Figure 1:
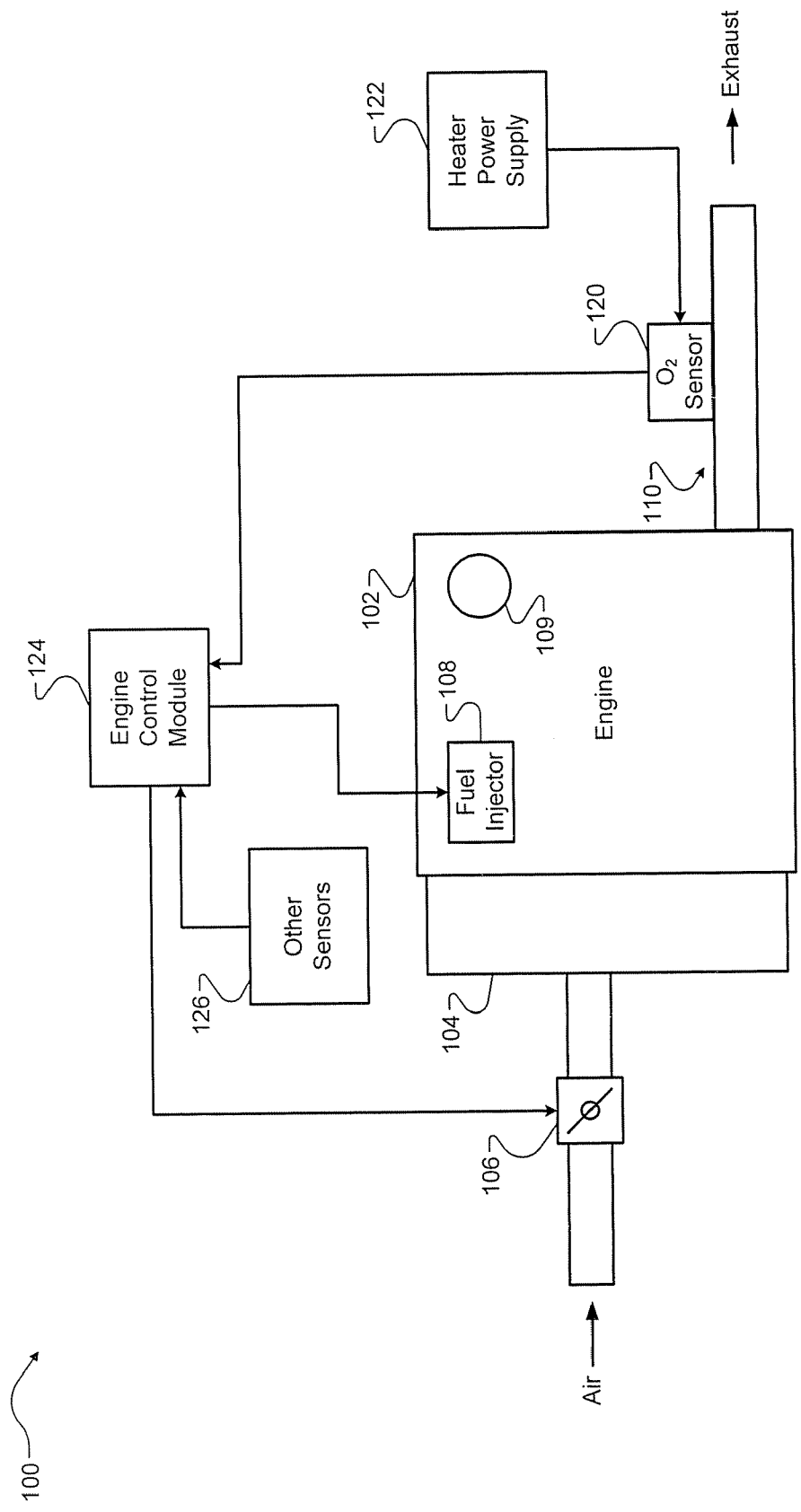
FIG. 1 is a functional block diagram of an engine system according to the prior art.

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module refers to an Application Specific Integrated Circuit (ASIC), an electronic circuit, a processor (shared, dedicated, or group) and memory that execute one or more software or firmware programs, a combinational logic circuit, and/or other suitable components that provide the described functionality.

An engine's emissions may be increased during startup. This may be because an engine controller cannot reliably control the air-fuel mixture of the engine in a closed-loop mode before the output of an oxygen sensor is reliable. Accurately determining when the output of the oxygen sensor is reliable will allow the engine controller to begin performing closed-loop control of the air-fuel mixture at the earliest possible time. This may reduce the engine's emissions.

According to the prior art, the output of the oxygen sensor is assumed to be reliable at a predetermined time after starting the engine. The predetermined time may be lengthy to ensure that the output of the oxygen sensor will be reliable in most circumstances. However, the output of the oxygen sensor may be reliable before the predetermined time under some circumstances (e.g., when the exhaust system is already warm upon starting). This may unnecessarily delay the engine controller in performing closed-loop control of the air-fuel mixture. Under other circumstances (e.g., when the exhaust system is experiencing extreme cold upon startup), the output of the oxygen sensor may be unreliable at the end of the predetermined time. This may cause the engine controller to incorrectly control the air-fuel mixture because the output of the oxygen sensor is not yet reliable.

In various implementations, the predetermined time may be started, after engine startup, by properties of the output of the oxygen sensor. These properties may vary based upon the exhaust conditions, but they may not be an accurate indicator of reliability. Accordingly, the predetermined time may be started too early under some exhaust system conditions and too late under other exhaust system conditions.

The reliability of the output of the oxygen sensor may be determined based upon an analysis of a pumping current that results from applying a bias voltage to the output of the oxygen sensor. This pumping current is an accurate indicator of the reliability of the output of the oxygen sensor. Determining the reliability of the output of the oxygen sensor based upon the pumping current may allow the engine controller to begin performing closed-loop control at the earliest possible time.

Figure 2:
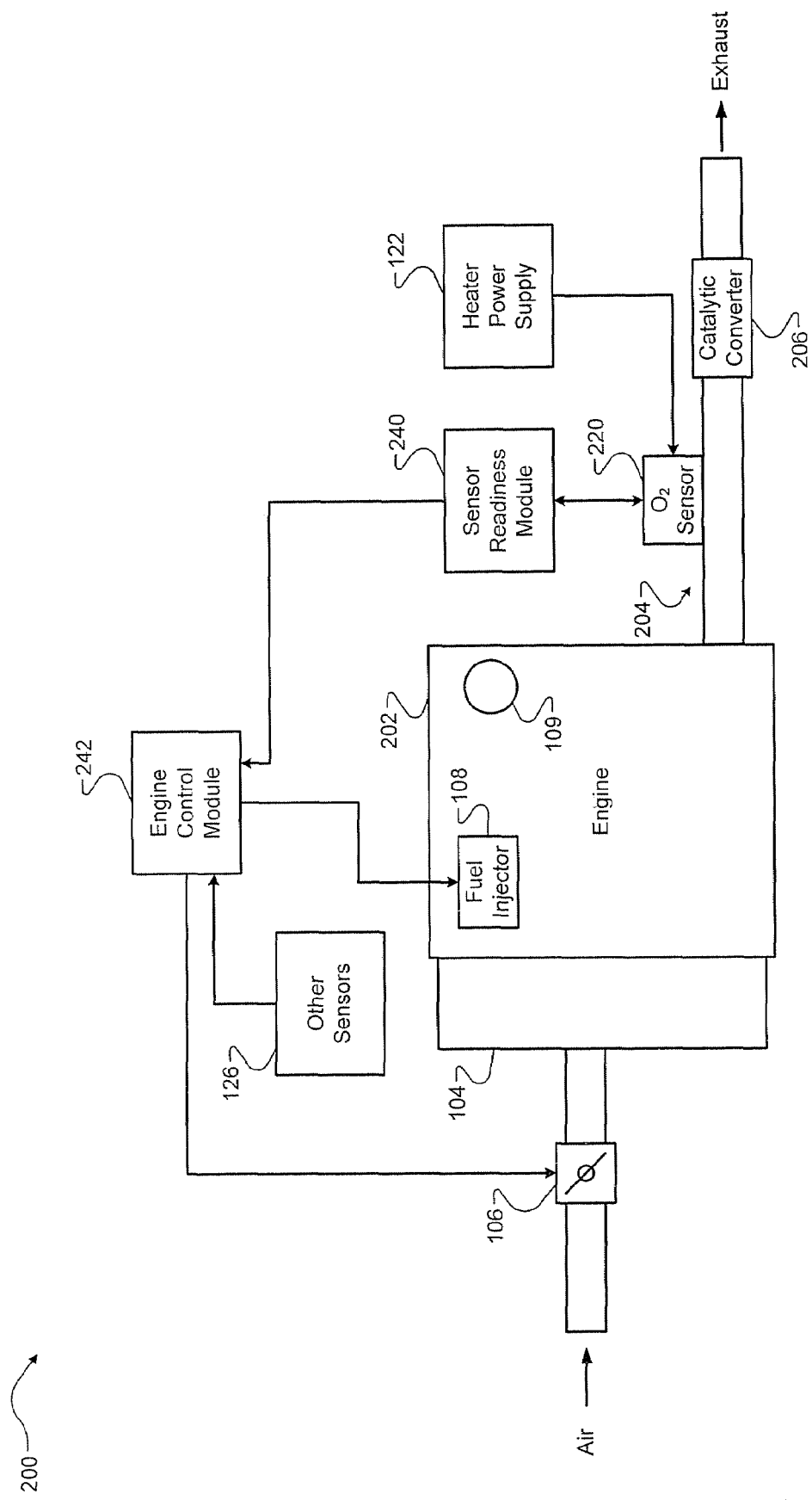
FIG. 2 is a functional block diagram of an exemplary engine system according to the principles of the present disclosure.

Referring now to FIG. 2, a functional block diagram of an exemplary engine system 200 is presented. Air is drawn into an engine 202 through the intake manifold 104. The volume of air is varied by the throttle valve 106. The air is mixed with fuel from one or more fuel injectors 108 to form an air-fuel mixture. The air-fuel mixture is combusted within one or more cylinders 109, and the resulting exhaust gas is expelled from the cylinder 109 to an exhaust system 204.

The exhaust system 204 includes a catalytic converter 206 and an oxygen sensor 220. Although the oxygen sensor 220 is depicted upstream of the catalytic converter 206, the oxygen sensor 220 may alternatively be disposed downstream of the catalytic converter 206. In various implementations, the oxygen sensor 220 may be a switching oxygen sensor, which may be a planar-type or a conical-type switching oxygen sensor.

The oxygen sensor 220 includes a sensing element, which may be made of, for example, a combination of ceramic and metallic materials. In various implementations, the metallic materials may include titanium, zirconium, platinum, and/or other metallic materials. A voltage is created at the sensing element of the oxygen sensor 220 based upon the concentration of oxygen in the exhaust gas. In various implementations, this voltage forms the output of the oxygen sensor 220.

When the temperature of the oxygen sensor 220 is below an operating temperature range, the output of the oxygen sensor 220 may be unreliable. For example only, the operating temperature range may be approximately 300° C.-400° C. Upon starting the engine 202, the temperature of the oxygen sensor 220 is likely below the operating temperature range. Accordingly, the output of the oxygen sensor 220 is likely unreliable upon starting the engine 202.

The oxygen sensor 220 may include a heater, which receives power from the heater power supply 122. The power may be delivered by, for example, an alternating current (AC) signal, a direct current (DC) signal, and/or a pulse width modulation (PWM) signal. For example only, the power may be delivered by a 12 V DC signal. The heater may bias the temperature of the oxygen sensor 220 to within the operating temperature range.

A sensor readiness module 240 utilizes the pumping current ability of the oxygen sensor 220 to determine whether the output of the oxygen sensor 220 is reliable. The sensor readiness module 240 applies a bias voltage to the sensing element of the oxygen sensor 220. In various implementations, the sensor readiness module 240 may apply the bias voltage upon startup of the engine 202. The bias voltage applied to the sensing element of the oxygen sensor 220 causes a pumping current to flow. As the oxygen sensor 220 warms up, the pumping current may increase.

The sensor readiness module 240 measures the pumping current and compares the pumping current with a calibratable pumping current threshold. In various implementations, the pumping current threshold may be set to correspond to a temperature at which the output of the oxygen sensor 220 is reliable. For example, this temperature may be the lowest temperature within the operating temperature range.

The sensor readiness module 240 determines that the output of the oxygen sensor 220 is reliable once the pumping current measurement exceeds the pumping current threshold. The sensor readiness module 240 disconnects the bias voltage from the sensing element of the oxygen sensor 220 once the output of the oxygen sensor 220 is determined to be reliable.

An engine control module (ECM) 242 may receive the output of the oxygen sensor 220 and signals from the other sensors 126. The ECM 242 may use the output of the oxygen sensor 220 in performing closed-loop control of the air-fuel mixture of the engine 202 once the output of the oxygen sensor 220 is reliable.

Figure 3:
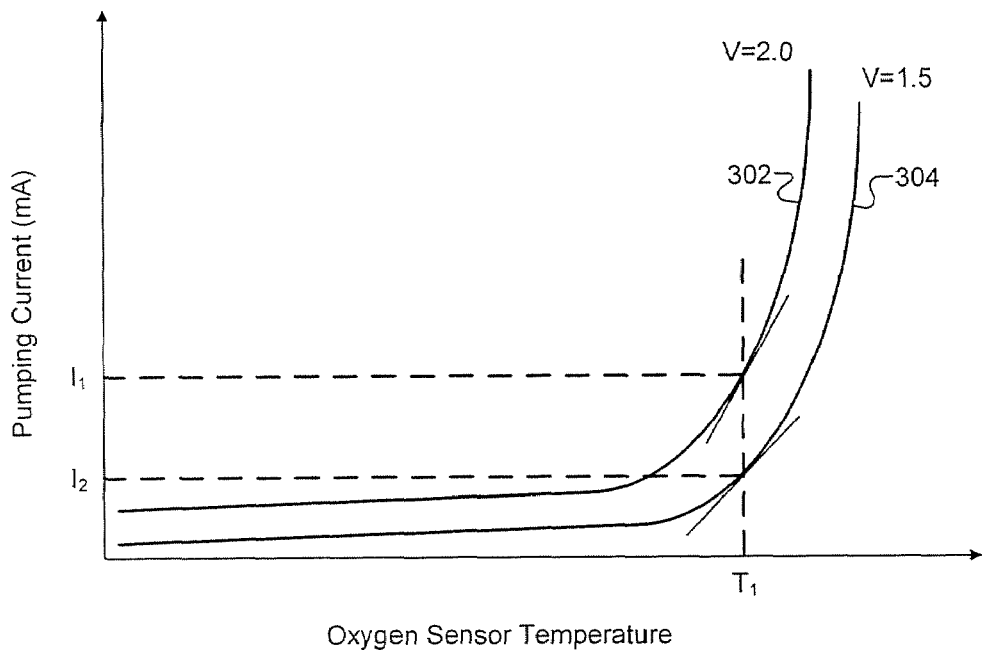
FIG. 3 is a graphical plot depicting pumping current versus temperature of an oxygen sensor according to the principles of the present disclosure.

Referring now to FIG. 3, a graphical plot depicting pumping current versus temperature of the oxygen sensor 220 is presented. Traces 302 and 304 depict exemplary relationships between pumping current and temperature of the oxygen sensor 220 where the bias voltage applied to the sensing element is 2.0 V and 1.5 V, respectively. Although the traces 302 and 304 are shown as exponential, the relationship between pumping current and temperature may be linear, parabolic, or any arbitrary relationship.

The output of the oxygen sensor 220 may be reliable when the temperature of the oxygen sensor 220 is above a predetermined temperature, such as temperature $T_1$. In various implementations, a pumping current threshold may be chosen that corresponds to the temperature at which the output of the oxygen sensor 220 becomes reliable.

For the traces 302 and 304, the pumping currents when the temperature of the oxygen sensor 220 is $T_1$ and the bias voltage is 2.0 V and 1.5 V are $I_1$ and $I_2$, respectively. Although DC bias voltages of 2.0 V and 1.5 V are depicted, the bias signal applied to the sensing element may be larger or smaller and may include an AC voltage, a PWM signal, or any other signal.

Fluctuations of the pumping current, such as may be caused by noise, may result in the pumping current crossing the pumping current threshold prematurely as compared to the smooth traces 302 and 304. The bias voltage applied to the sensing element of the oxygen sensor 220 may be chosen to create a larger rate of change of the pumping current as the pumping current approaches the pumping current threshold. In such implementations, a large amount of noise will be required to cause the pumping current to prematurely cross the pumping current threshold.

In various implementations, a larger bias voltage may create a larger rate of change of the pumping current near the pumping current threshold. For example, at temperature $T_1$, the rate of change of the pumping current is larger when the bias voltage is 2.0 V (i.e., at $I_1$) than when the bias voltage is 1.5 V (i.e., at $I_2$).

Figure 4:
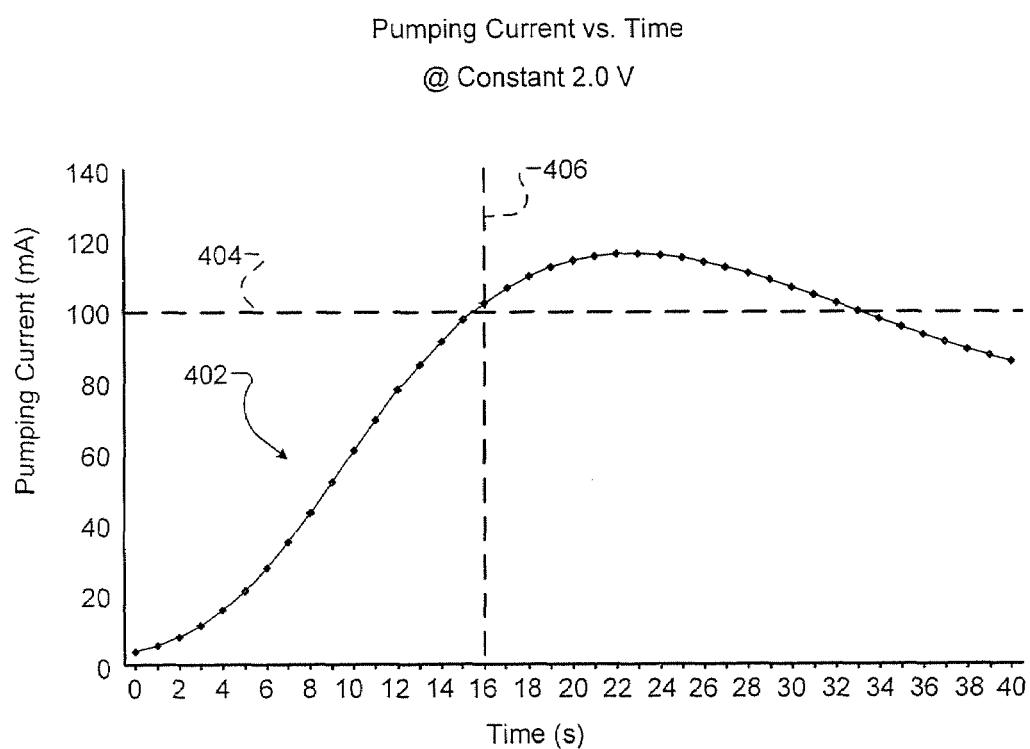
FIG. 4 is a graphical plot depicting an exemplary trace of a pumping current of an oxygen sensor according to the principles of the present disclosure.

Referring now to FIG. 4, a graphical plot depicting an exemplary trace 402 of the pumping current of the oxygen sensor 220 versus time is presented. Time zero represents the time at which the sensor readiness module 240 applies the bias voltage to the sensing element of the oxygen sensor 220. In various implementations, time zero may also represent the time at which the engine 202 is started from a cold state.

The output of the oxygen sensor 220 may be unreliable until the temperature of the oxygen sensor 220 reaches a predetermined temperature, such as the temperature $T_1$ of FIG. 3. As the engine 202 runs, the oxygen sensor 220 warms up and the pumping current increases. The sensor readiness module 240 measures the pumping current and determines whether the output of the oxygen sensor 220 is reliable based upon a comparison of the pumping current with a pumping current threshold.

The sensor readiness module 240 may measure the pumping current at a predetermined sampling rate. Although a sampling rate of one sample per second is shown, the sensor readiness module 240 may sample the pumping current more or less frequently and the sampling rate may change with time. In various implementations, the sensor readiness module 240 may sample the pumping current more frequently as the pumping current approaches the pumping current threshold.

Dashed line 404 represents an exemplary pumping current threshold. For example only, the pumping current threshold may be set to 100 mA. The output of the oxygen sensor 220 may be determined to be reliable once the pumping current 402 exceeds the pumping current threshold 404. Dashed line 406 represents an exemplary time when the pumping current exceeds the pumping current threshold. Accordingly, the dashed line 406 represents the time at which the output of the oxygen sensor 220 may be reliable.

For example only, FIG. 4 indicates that the output of the oxygen sensor 220 may be reliable sixteen (16) seconds after the engine 202 is started from a cold state. Even for the same engine, the output of the oxygen sensor 220 may be reliable at an earlier time when the engine 202 is started from a warm state.

Figure 5:
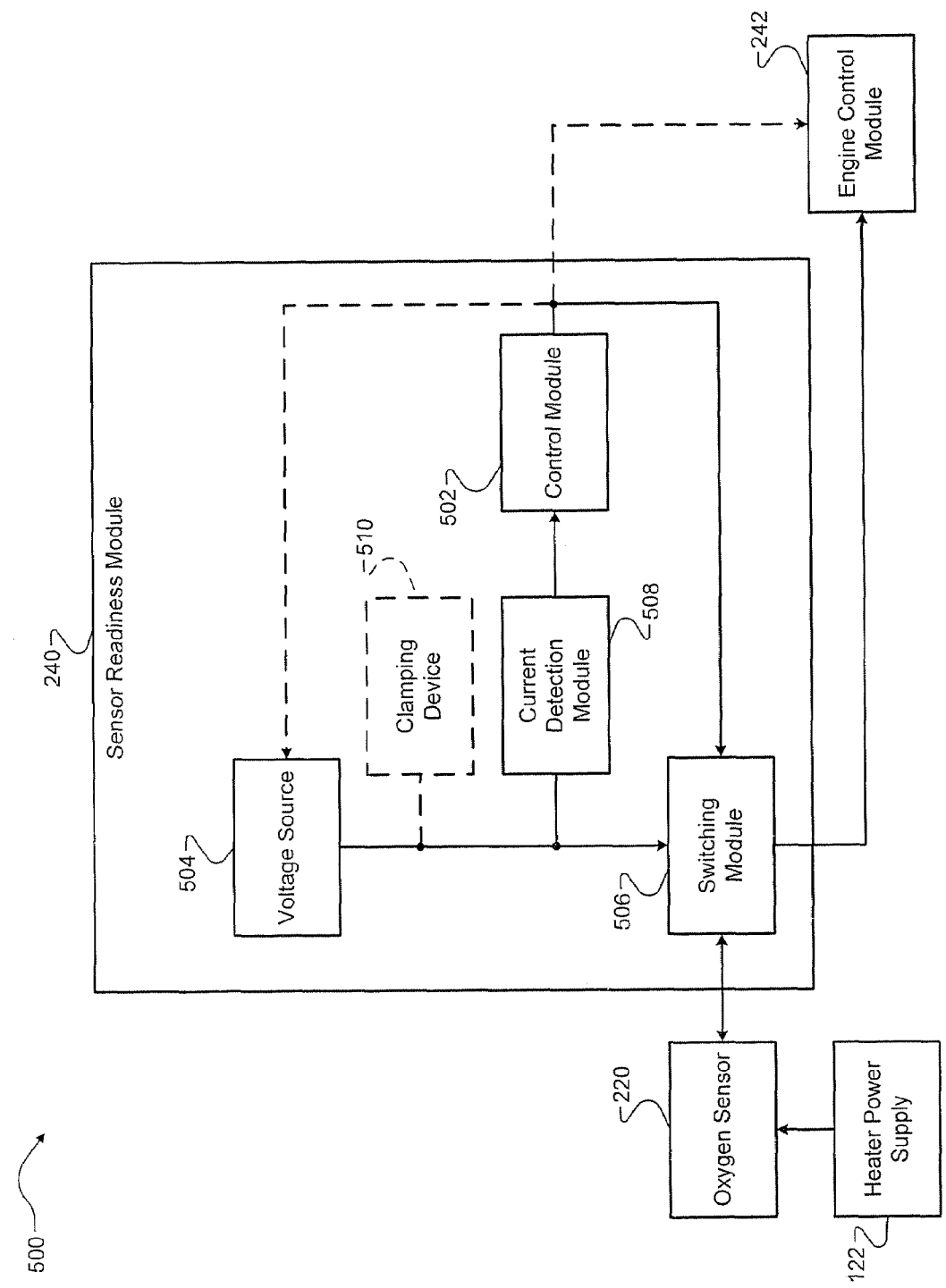
FIGS. 5-5A are exemplary block diagrams of exemplary oxygen sensor systems according to the principles of the present disclosure.

Referring now to FIG. 5, a block diagram of an exemplary oxygen sensor system 500 is presented. The sensor readiness module 240 includes a control module 502, a voltage source 504, a switching module 506, and a current detection module 508. The control module 502 generates a readiness signal, which indicates whether the output of the oxygen sensor 220 is reliable.

The voltage source 504 produces a calibratable bias signal. The bias signal may be a digital signal or an analog signal and may include a voltage, a current, and/or any other signal. For example only, the bias signal may be set to a voltage of 2.0 V or 1.5 V. In various implementations, the voltage source 504 may receive the readiness signal and may stop producing the bias signal when the readiness signal indicates that the output of the oxygen sensor 220 is reliable.

The switching module 506 receives the readiness signal and the bias signal of the voltage source 504. The switching module 506 selectively applies the bias signal of the voltage source 504 to the sensing element of the oxygen sensor 220 based upon the readiness signal. In various implementations, the switching module 506 applies the bias signal to the sensing element of the oxygen sensor 220 until the readiness signal indicates that the output of the oxygen sensor 220 is reliable. The switching module 506 may include a semiconductor switch, a relay, a transistor, or any other suitable switching device.

The sensor readiness module 240 may include an optional clamping device 510 to avoid damaging the oxygen sensor 220. The clamping device 510 limits the bias signal applied to the sensing element of the oxygen sensor 220 and/or the pumping current. The current detection module 508 measures the pumping current and generates a pumping current signal that indicates the magnitude of the pumping current. The pumping current signal may be a digital signal or an analog signal and may include a voltage, a current, and/or any other signal.

The control module 502 determines whether the output of the oxygen sensor 220 is reliable based upon analysis of the pumping current signal. In various implementations, the control module 502 may determine that the output of the oxygen sensor 220 is reliable once the pumping current signal exceeds the pumping current threshold.

The control module 502 generates the readiness signal indicating whether the output of the oxygen sensor 220 is reliable. In various implementations, the readiness signal may be a digital signal or an analog signal and may include a voltage, a current, and/or any other signal. The switching module 506 connects the output of the oxygen sensor 220 to the ECM 242 once the readiness signal indicates that the output of the oxygen sensor 220 is reliable.

The ECM 242 may use the output of the oxygen sensor 220 when the output of the oxygen sensor 220 is available. The ECM 242 may receive the readiness signal, which indicates to the ECM 242 whether the output of the oxygen sensor 220 is available. In various implementations, the ECM 242 receives a predetermined output signal from the switching module 506, such as zero Volts, until the output of the oxygen sensor 220 is available. The ECM 242 may determine that the output of the oxygen sensor 220 is available when the signal from the switching module 506 deviates from the predetermined output signal. This deviation can be assumed to be caused by the switching module 506 connecting the ECM 242 to the output of the oxygen sensor 220.

Figure 5A:
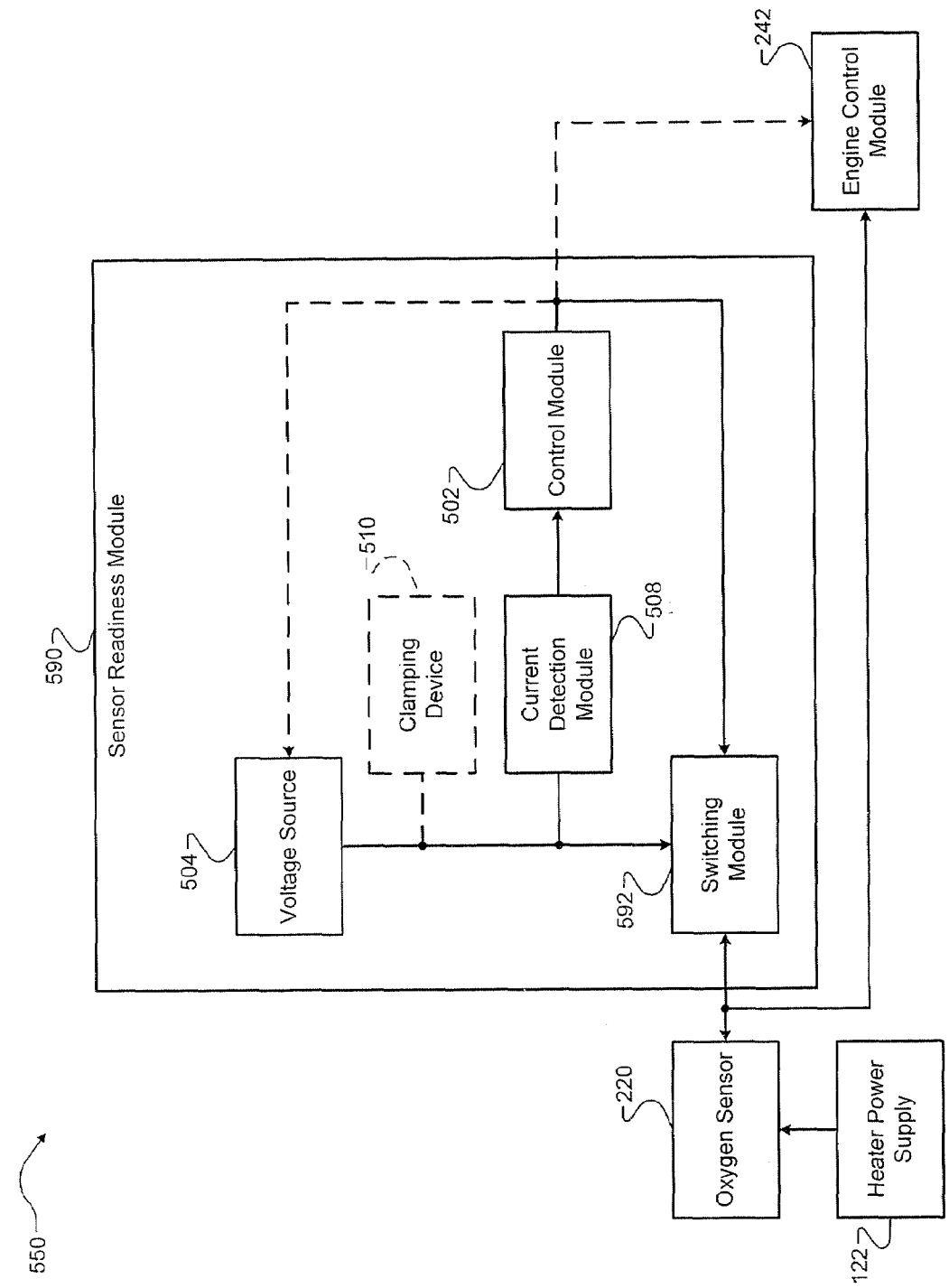

Referring now to FIG. 5A, a block diagram of another exemplary oxygen sensor system 550 is presented. The oxygen sensor system 550 includes an exemplary sensor readiness module 590, which includes a switching module 592. The switching module 592 receives the readiness signal from the control module 502 and applies the bias signal of the voltage source 504 to the sensing element of the oxygen sensor 220. The switching module 592 disconnects the bias signal from the sensing element once the readiness signal indicates that the output of the oxygen sensor 220 is reliable.

The ECM 242 receives the output of the oxygen sensor 220 (i.e., the voltage at the sensing element of the oxygen sensor 220). The ECM 242 may then begin using the output of the oxygen sensor 220 when the output of the oxygen sensor 220 is reliable. In various implementations, the ECM 242 receives the readiness signal, which indicates when the output of the oxygen sensor 220 is reliable.

In various implementations, the ECM 242 may determine that the output of the oxygen sensor 220 is reliable when the output of the oxygen sensor 220 deviates from the bias signal of the voltage source 504. This deviation can be assumed to be caused by the switching module 592 disconnecting the voltage source 504 from the output of the oxygen sensor 220.

Figure 6:
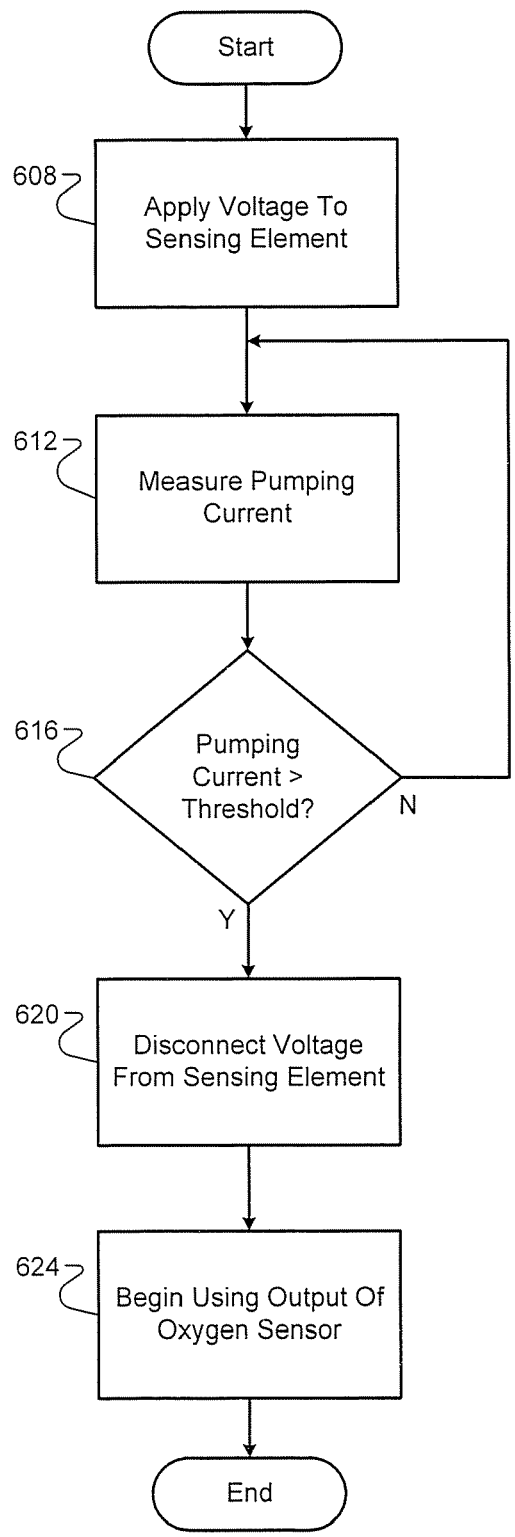
FIG. 6 is a flowchart depicting exemplary steps performed by a sensor readiness module according to the principles of the present disclosure.

Referring now to FIG. 6, a flowchart depicting exemplary steps performed by a sensor readiness module is presented. Control begins in step 608, where control applies a bias voltage to the sensing element of the oxygen sensor 220. In various implementations, control begins upon startup of the engine 202. The bias voltage applied to the sensing element causes a pumping current to flow based upon the temperature of the oxygen sensor 220. Control continues in step 612, where control measures the pumping current, and control continues in step 616.

In step 616, control determines whether the pumping current is greater than the pumping current threshold. If the pumping current is greater than the pumping current threshold, control continues in step 620; otherwise, control returns to step 612. In step 620, control disconnects the bias voltage from the sensing element of the oxygen sensor 220. Control continues in step 624, when control begins using the output of the oxygen sensor 220. In various implementations, control may use the output of the oxygen sensor 220 in performing closed-loop control of the air-fuel mixture. Control then ends.

Those skilled in the art can now appreciate from the foregoing description that the broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. An oxygen sensor readiness module comprising:
   a voltage source that selectively produces a bias signal, which is applied to a sensing element of an oxygen sensor to generate a pumping current;
   a current detection module that measures said generated pumping current of said oxygen sensor; and
   a control module that generates a readiness signal based upon a comparison of said generated pumping current with a pumping current threshold.

2. The oxygen sensor readiness module of claim 1 wherein said oxygen sensor is a switching oxygen sensor.

3. The oxygen sensor readiness module of claim 1 wherein said oxygen sensor is one of a planar type switching oxygen sensor and a conical type switching oxygen sensor.

4. The oxygen sensor readiness module of claim 1 further comprising a switching module that applies said bias signal to said sensing element of said oxygen sensor until said readiness signal is received.

5. The oxygen sensor readiness module of claim 1 further comprising a clamping device that limits at least one of said bias signal and said pumping current.

6. The oxygen sensor readiness module of claim 1 wherein said pumping current threshold is set to correspond to a temperature at which an output of said sensing element of said oxygen sensor is reliable.

7. The oxygen sensor readiness module of claim 1 wherein said bias signal is a direct current (DC) voltage.

8. The oxygen sensor readiness module of claim 1 wherein said voltage source stops producing said bias signal after said readiness signal is received.

9. An oxygen sensor system comprising:
   the oxygen sensor readiness module of claim 1;
   the oxygen sensor; and
   an engine control module that selectively uses an output of said sensing element of said oxygen sensor.

10. The oxygen sensor system of claim 9 wherein said engine control module uses said output based upon said readiness signal.

11. The oxygen sensor system of claim 9 wherein said engine control module ignores said output until said engine control module receives said readiness signal.

12. The oxygen sensor system of claim 9 wherein said engine control module uses said output in performing closed-loop control of an air-fuel mixture.

13. The oxygen sensor system of claim 9 further comprising a switching module that connects said sensing element of said oxygen sensor to said engine control module based upon said readiness signal.

14. The oxygen sensor system of claim 13 wherein said engine control module uses said output after said bias signal no longer appears at said sensing element of said oxygen sensor.

15. A method of determining readiness of an oxygen sensor, comprising:
   selectively producing a bias signal;
   applying said bias signal to a sensing element of an oxygen sensor to generate a pumping current;

measuring said generated pumping current of said oxygen sensor;

comparing said pumping current with a pumping current threshold; and generating a readiness signal based upon said comparing.

16. The method of claim 15 further comprising selectively using an output of said oxygen sensor in controlling an engine based upon said readiness signal.

17. The method of claim 15 further comprising ignoring an output of said oxygen sensor until said readiness signal is generated.

18. The method of claim 15 further comprising connecting said sensing element of said oxygen sensor to an engine control module based upon said readiness signal.

19. The method of claim 15 further comprising using an output of said oxygen sensor in controlling an engine after said bias signal no longer appears at said sensing element of said oxygen sensor.

20. The method of claim 15 further comprising applying said bias signal to said sensing element of said oxygen sensor until said readiness signal is generated.

21. The method of claim 15 further comprising limiting at least one of said bias signal and said pumping current.

22. The method of claim 15 further comprising stopping producing said bias signal after said readiness signal is generated.

* * * * *